United States Patent [19]

Homsy et al.

[11] Patent Number: 4,778,472
[45] Date of Patent: Oct. 18, 1988

[54] IMPLANT FOR RECONSTRUCTION OF TEMPOROMANIBULAR JOINT

[75] Inventors: Charles A. Homsy; John W. Tellkamp, both of Houston, Tex.; John N. Kent, Metairie, La.

[73] Assignee: Vitek, Inc., Houston, Tex.

[21] Appl. No.: 939,558

[22] Filed: Dec. 9, 1986

Related U.S. Application Data

[63] Continuation-in-part of Ser. No. 728,820, Apr. 30, 1985, abandoned.

[51] Int. Cl.$^4$ .............................................. A61F 2/30
[52] U.S. Cl. ...................................................... 623/18
[58] Field of Search ...................... 623/18, 19, 20, 21, 623/22, 23; 128/92 R

[56] References Cited

U.S. PATENT DOCUMENTS

D. 248,665  7/1978  Homsey et al. ............... 623/18 X
3,140,712  7/1964  Hunter .............................. 623/18 X
3,178,728  4/1965  Christensen ....................... 623/18
4,693,722  9/1987  Wall .................................. 623/18

Primary Examiner—Richard J. Apley
Assistant Examiner—Alan W. Cannon
Attorney, Agent, or Firm—Michael P. Breston

[57] ABSTRACT

The surgical TM joint implant has two-parts: a first part which covers or replaces the natural glenoid fossa and articular eminence of a natural TM joint, and a second part which replaces the natural condylar head of the joint. The first part includes a plate having a fossa cavity defined by a relatively deep concave portion and an anteriorly located concavo-planar portion. The second part has a condylar head defining a convexo-planar, articular face for engaging the concavo-planar surface and establishing therewith a planar contact area which minimizes the unit stress transmitted between the first and second parts, thereby providing for an even load distribution between their engaged planar surfaces.

5 Claims, 2 Drawing Sheets

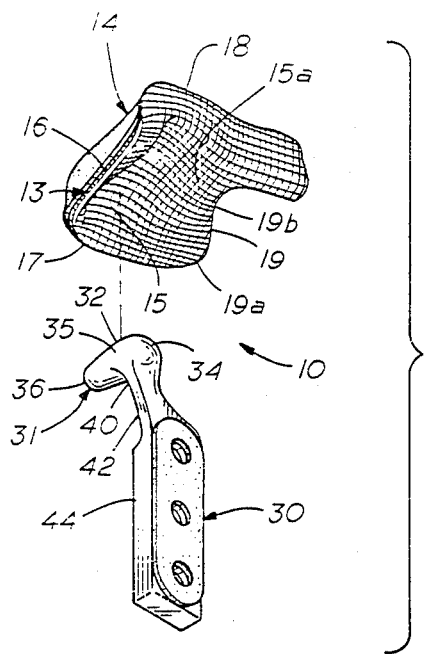
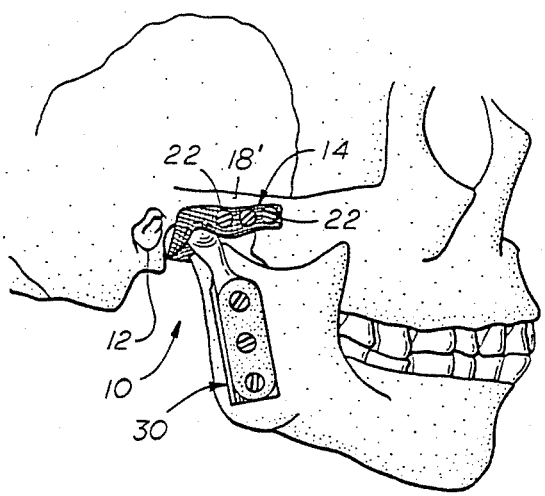
FIG. 1
FIG. 2
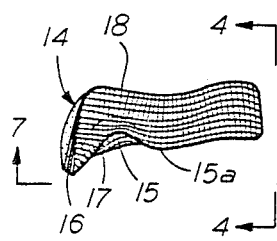
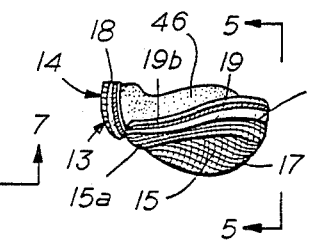
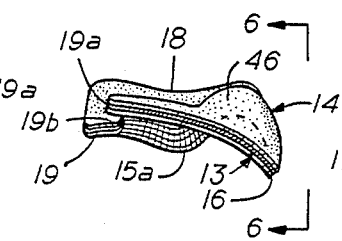
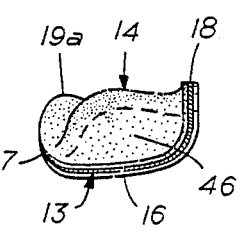
FIG. 3   FIG. 4   FIG. 5   FIG. 6
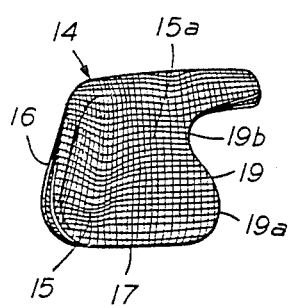
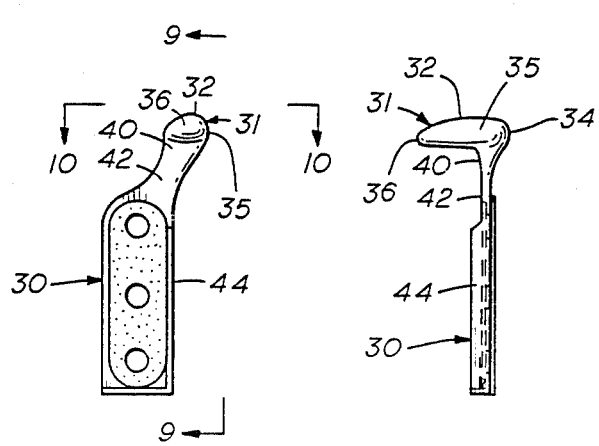
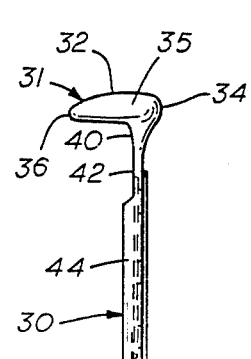
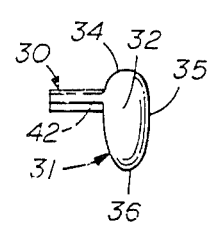
FIG. 7   FIG. 8   FIG. 9
FIG. 10

IMPLANT FOR RECONSTRUCTION OF TEMPOROMANIBULAR JOINT

BACKGROUND OF THE INVENTION

This application is a continuation-in-part of application Ser. No. 06/728,820, filed 04/30/1985, now abandoned.

1. Field of the Invention

The invention relates to implants for the temporomandibular joint which consists of the glenoid fossa, the condylar head of the mandible, the mandibular disc, and muscle attachments.

2. Description of the Prior Art

Patients with severe destruction of the temporomandibular joint (TMJ) anatomy from rheumatoid arthritis, osteoarthritis, tumors, and trauma all manifest significant functional impairment and often pose difficult challenges in joint reconstruction.

Christensen (U.S. Pat. No. 3,178,728) made castings of chrome-cobalt to cover the glenoid fossa including the mandibular fossa and the articular eminence. Twenty castings were available for each operative procedure from which to select a fit within the patient's natural glenoid fossa.

For surgical application of a fossa prosthesis sized and contoured to fit within the mandibular fossa and to overlay the articular eminence, approximately 10–15 prostheses of differing sizes and contours are required. The time required to surgically apply a prosthesis which is of such a size and contour as to fit within the mandibular fossa and overlay the articular eminence is of substantial duration.

Morgan (U.S. Pat. No. 3,579,643) believed that a prosthesis which is sized and shaped to fit or cover the entire glenoid fossa, including the mandibular fossa and the articular eminence, possessed a number of serious disadvantages. Specifically, he believed that the presence of such a fossa prosthesis between the head of the condyle and the mandibular fossa will disturb the normal relationship between the head of the condyle and mandibular fossa, resulting in disruption of normal jaw function or alteration of the occlusion or bite.

Morgan's prosthesis covered the articular eminence only and consisted of a rim extending anteriorly with a lateral aspect. By providing holes in the rim, the artificial articular eminence may be secured to the zygoma with suitable screws.

By analyzing many artificial articular eminences, Morgan contoured a single right and a single left artifical articular eminence. Morgan believed that because his prosthesis did not overlay or contact the mandibular fossa, one right and one left universal appliance could be designed.

But, the use of both glenoid fossa and condylar prostheses for total TMJ reconstruction have been advocated by others to restore lost condylar height. Recently, metallic condylar prostheses and polymer glenoid fossa implants for total joint replacement became popular for many cases of ankylosis.

A custom polymer glenoid fossa prosthesis was developed by Vitek, Inc., Houston, Tex., to complement the natural anatomy of the TMJ. It mimicked the slope of the articular eminence and the oval shape of the glenoid fossa and its articulating surface.

The glenoid fossa prosthesis was made of three layers. It was a multiple laminate construction in which the superior layer was PROPLAST I (PTFE-graphite) implant material, the middle layer was TEFLON FEP (fluorinated ethylene propylene) polymer with an embedded polyamide or metal mesh, and the most inferior layer or articulating surface was fabricated of fused TEFLON PTFE (polytetrafluoroethylene) polymer reinforced with graphite fiber.

The fossa prosthesis covered the mandibular fossa, but it did not extend fully over the articular eminence. Neither did it adequately protect the external auditory canal. This multi-component construction was complex and not easily adaptable to reproducible manufacturing procedures.

A less complex bilaminate custom structure was then developed by Vitek, Inc. PROPLAST II (polytetrafluoroethylene polymer with aluminum oxide) implant material was selected to interface with the bony fossa, since it could be easily carved and modified to variable anatomic situations. The mating material was surgical chrome-cobalt-molybdenum alloy used to manufacture the TMJ condylar prosthesis.

The custom prosthesis included only two layers: a superior layer of PROPLAST II for ease of carving, adaptability, and stabilization by tissue ingrowth, and an inferior layer of TEFLON FEP with polyamide mesh reinforcement for suitable articulation with a natural or metallic condyle.

It was found that such a fossa prosthesis was characterized by insufficient force distribution. Poor distribution of stress may lead to bone resorption, fibrous encapsulation, loosening, extrusion and failure of the material, and dislocation of the prosthesis.

Long term stabilization, favorable distribution of articulating forces without slippage are the desirata.

It is a primary object of this invention to minimize high stress concentration during articulation of metallic or natural condyle with the fossa implant.

It is another object to improve the medial lateral axis of the fossa cavity for better condyle head articulation, to reduce the overall size, to minimize trimming time, to move the protective flange slightly anterior to avoid impingement of soft tissue over the external auditory canal. The glenoid fossa prosthesis of the present invention optimizes the TMJ function through improved adaptability during surgery. It can be surgically applied in a short period of time because one fossa prosthesis will fit many patients.

It is a further object to provide a condylar prosthesis having improved articulation with the fossa prosthesis, and being characterized by a smaller, more laterally-located condylar head with an increased articulating surface area.

SUMMARY OF THE INVENTION

The surgical TM joint implant has two-parts: a first part which covers or replaces the natural glenoid fossa and articular eminence of a natural TM joint, and a second part which replaces the natural condylar head of the joint. The first part includes a plate having a fossa cavity defined by a relatively deep concave portion over the glenoid fossa which blends into a anteriorly located concavo-planar portion which in turn blends into convexo and planar portions over the articular eminence. The second part has a condylar head defining a convexo-planar, articular face for engaging the concavo-planar surface and establishing therewith a planar contact area which minimizes the unit stress transmitted between the first and second parts, thereby providing for an even load distribution between their engaged planar surfaces and minimizing stress concentrations.

The plate is preferably shaped to fully cover the articular eminence and to protect the external acoustic meatus against external pressure.

BRIEF DESCRIPTION OF THE DRAWINGS

FIG. 1 is an exploded perspective view of the preferred forms of the fossa and condyle head prostheses in accordance with the invention;

FIG. 2 is a side elevational view of a human skull carrying the artificial prostheses of FIG. 1;

FIG. 3 is a side view of the fossa prosthesis shown in FIG. 1;

FIGS. 4-7 are views taken on lines 4—4 through 7—7 on FIGS. 3, 4, 5 and 3, respectively;

FIG. 8 is a side plan view of the glenoid head prosthesis shown in FIG. 1;

FIG. 9 is an elevational view taken on line 9—9 of FIG. 8;

FIG. 10 is a top view taken on line 10—10 of FIG. 8;

FIG. 11 shows the condyle head near closed bite closure, and FIG. 12 shows the condyle head when the jaws are fully engaged.

DESCRIPTION OF PREFERRED EMBODIMENTS

Figure 18:
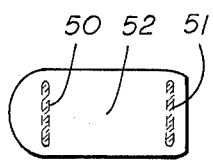
FIG. 18 is a plan view of the concentrated load-transfer lines between the known condyle head prosthesis when it is in engagement with the known fossa prosthesis, as shown in FIG. 15.
Figure 14:
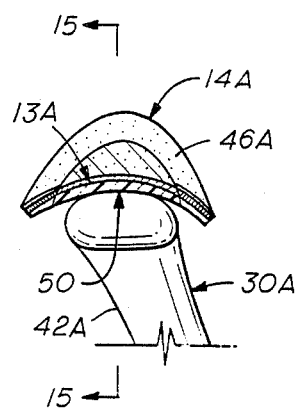
FIG. 14 is a view taken on line 14—14 of FIG. 15, which shows applicant's above-mentioned, already-known, second type of fossa prosthesis in engagement with the prior condyle head prosthesis when it is in a position similar to that of FIG. 11.
Figure 15:
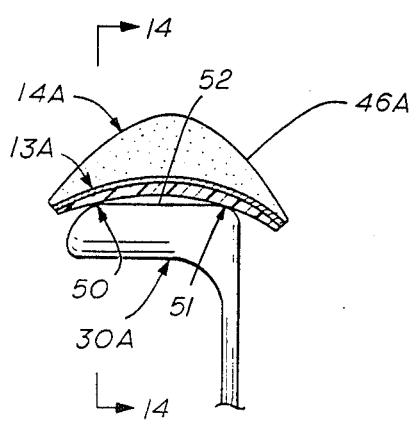
FIG. 15 is a view taken on line 15—15 of FIG. 14.
Figure 16:
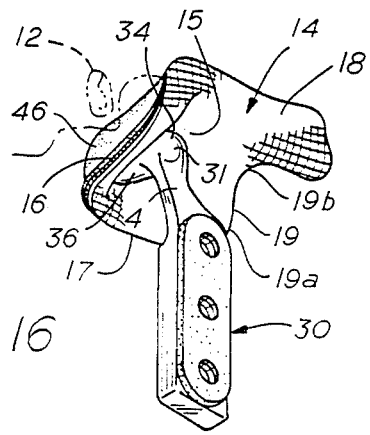
FIG. 16 is an enlarged perspective view, similar to FIG. 2, showing the novel condyle head prosthesis in engagement with the novel fossa prosthesis.

The invention will be described with general reference to FIGS. 1-13 and 16-17. In FIGS. 14-15 and 18, which illustrate applicant's prior fossa and condylar head prostheses, the same numerals followed by the letter "A" are used to designate corresponding parts of FIGS. 1-13 and 16.

The novel composite prosthesis 10 (FIGS. 1-2, 16) of this invention consists of a condyle prosthesis 30 and of a glenoid fossa prosthesis 14, which respectively constitute the ball and socket portions of a reconstructed TM joint.

Figure 11:
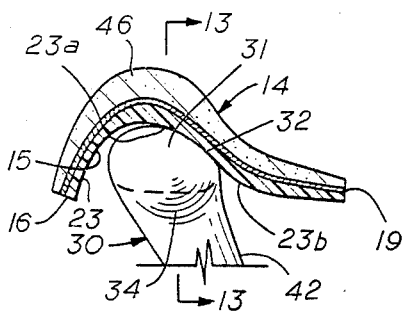
FIGS. 11 and 12 show a partial side elevational view of the condyle prosthesis and a sectional view of the fossa prosthesis.
Figure 12:
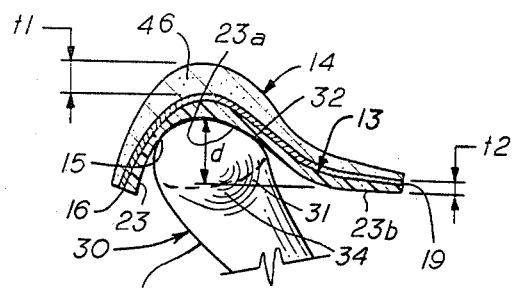
Figure 17:
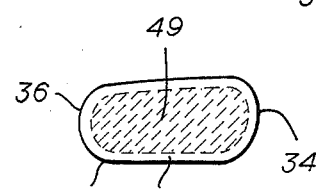
FIG. 17 shows the planar contact surface between the novel condyle head and the novel fossa prosthesis when the jaws are near or at full engagement, as shown in FIG. 11.
Figure 13:
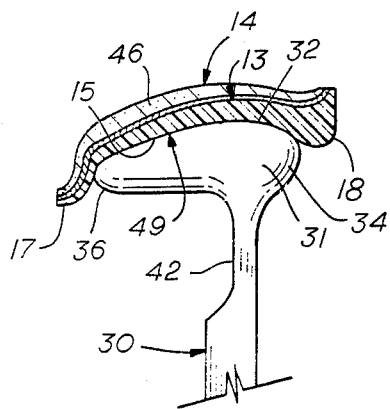
FIG. 13 is a view taken on line 13—13 of FIG. 11.

The condyle head prosthesis 30 (FIGS. 8-9, 11-14) is made of a surgical, chrome-cobalt-molybdenum alloy and comprises a condyle head 31 which is provided with a critical load-transmitting, convexo-planar, articular face 32 (FIG. 11). A heel 34 extends backwardly and a toe 36 extends forwardly from face 32. An oval sole 35 (FIGS. 1,9) follows and extends rearwardly from face 32 and smoothly blends at its opposite ends with the heel and toe. A bridge part 40 spans between face 32, heel 34, and toe 36. A neck 42 couples bridge 40 to shank 44.

Fossa prosthesis 14 is made of a superior layer 46 of PROPLAST (a registered TM of applicant) which is a tissue ingrowth promoting material (e.g., a composite of polytetrafluoroethylene polymer and aluminum oxide or synthetic hydroxylapatite), and of an inferior plate 13 of fluorinated ethylene propylene or ultra high molecular weight polyethylene polymer having an embedded polyamide mesh reinforcement therein.

Plate 13 is shaped to (1) fully cover the natural fossa cavity including the adjoining natural articular eminence, (2) to give the surgeon one left fossa prosthesis and one right fossa prosthesis generally fitting the TM joints of most patients, (3) to protect the external acoustic meatus 12 (FIG. 2) against external pressure and inhibit meatus 12 from post-operatively adhering to condyle head 31, and (4) to allow trimming of PROPLAST material for adaptation to specific fossa-eminence anatomy.

By using a single left and a single right fossa prostheses of 2 or 3 different sizes and with the ability to modify the PROPLAST surface and plate 13, the surgeon requires less operative time, while the implant manufacturer is relieved from the burden and expense of making large numbers of custom fossa and condylar prostheses based on individual X-rays.

Plate 13 (FIG. 1) has a fossa cavity 15 which is defined by posterior rim 16, medial rim 17, lateral rim 18, and anterior eminence rim 19. The posterior rim 16 sufficiently projects inferiorly of fossa cavity 15 to protect the external acoustic meatus 12. The protective posterior rim 16 is moved slightly anteriorly to avoid impingement of soft tissue over the external auditory canal.

Medial rim 17 smoothly joins the posterior rim 16 and likewise projects inferiorly to cover the medial aspect of the natural glenoid fossa and of the adjoining articular eminence. The anterior eminence rim 19 has an apex 19a and projects anteriorly and obliquely superiorly to cover the the remainder portion of the articular eminence. Eminence rim 19 is relieved at 19b to conform to the junction between the natural zygoma 18' and the natural articular eminence.

Lateral rim 18 extends superiorly to and is shaped to fit along the lateral extension of zygoma 18' (FIG. 2). Fossa cavity 15, anterior ridge 15a (FIGS. 4-5), anterior eminence rim 19, medial rim 17, and posterior rim 16 are shaped to offer minimum friction to the complex movements of condyle head 31 over fossa cavity 15. Rim 18 usually receives one or more screws 22 by means of which prosthesis 14 is initially attached to zygoma 18', whereas the tissue-ingrowth-promoting porous material provides permanent postoperative fixation for fossa prosthesis 14 within the TM joint.

There are three unique features which make the TM joint very complex: it is a non-stress and stress bearing joint, depending on the spacing between condyle head 31 and fossa cavity 15; it is a sliding hinge, and it is a bilateral joint, i.e., both the right and left sides of the joint should act in symmetry.

Therefore, fossa cavity 15 (FIGS. 11-12) is provided with a stress-bearing, articular surface defined by a relatively deep concave portion 23 beginning posteriorly, extending superiorly to an anteriorly-superiorly located concavo-planar portion 23a, and extending anteriorly to a convexo-planar portion 23b.

When the TM joint is within mid-opening to closed bite position (FIG. 11), the articular, load-transfer, convexo-planar face 32 of condylar head 31 engages the articular, load-receiving, concavo-planar surface 23a of fossa cavity 15 and establishes therewith a relatively wide planar contact area 49 (FIG. 17) which minimizes the unit stress (kg/cm$^2$) transmitted between prostheses 14 and 30 and provides for an even load distribution between their engaged planar sliding surfaces.

In articulating the mandible from closed bite position (FIG. 12) to nearly open bit position (FIG. 11), convexo-planar, load-transfer face 32 of condyle head 31 moves forwardly on deep concave surface 23, then the planar portion of face 32 slides, while exerting very strong pressure, over the planar portion of surface 23a, and then face 32 may move toward the convex portion of the convexo-planar surface 23b.

The convexo-planar articular face 32 and the concavo-planar surfaces 23a are shaped to maximize the extent of the contact area 49 and minimize wear, as condylar head 31 translates and rotates within fossa cavity 15.

It has been unexpectedly found that minimal stress concentration at the critically near closed bit position of the mandible (FIG. 11) is provided by maximizing the extent of planar contact area 49 between the planar portion of convexo-planar face 32 and the planar portion of concavo-planar surface 23a. As an additional benefit, fossa cavity 15 optimally distributes the significant lateral pressures to which it becomes subjected during jaw movements.

In sum, the engaging articular concavo-planar and convexo-planar surfaces 23a and 32, respectively, are shaped so as to better protect the natural fossa and auditory canal 12 (FIG. 2) from pressure, and to more evenly and efficiently distribute the forces transmitted through the planar contact area 49, especially near closed bite position (FIG. 11), which is the critical position corresponding to maximum load transmission through the reconstructed TM joint.

This is in contrast to what one would obtain from applicant's prior glenoid fossa prosthesis 14A and condyle prosthesis 30A (FIGS. 14–15). It will be readily seen that the external articular surface 42 of condyle head prosthesis 30A engages its opposite fossa plate 13A only along a pair of single-dimensional parallel lines 50 and 51 (FIG. 18), while the remainder of surface 52 between lines 50 and 51 is out of contact with plate 13A. As condyle head 30A translates and rotates over the fossa cavity defined by plate 13A, these parallel lines 50–51 also rotate, and for some positions of condyle head 30A lines 50–51 actually merge. Consequently, uneven and concentrated transfers of stress take place between condylar head prosthesis 30A and fossa prosthesis 14A. Such concentrated stresses are largest especially at near biting closure (FIG. 15) and can lead to great pain, bone resorption, fibrous encapsulation, loosening, extrusion, failure of the artificial fossa's material, and dislocation of the fossa and condyle prostheses within the TM joint.

It will be also noted that the overall size of the novel glenoid fossa prosthesis 14 is reduced as compared to prior fossa prosthesis 14A. Hence the trimming time required from the surgeon of fossa prosthesis 14 is minimized. Long term stabilization, favorable distribution of articular forces without slippage are obtained with the two-part prosthesis 10 of this invention.

In one embodiment, the maximum used thickness "t1" (FIG. 12) of the PROPLAST II coating 46 (FIG. 5) was within a range of 1–9 mm with preferred values of 4 m and 7 m, and the depth "d" of fossa cavity 15 had a range of 1 mm to 9 mm with preferred values of 3 mm and 6 mm. The thickness "t2" of plate 13 had a range between 1 mm and 4 mm with a preferred value of 2 mm.

What is claimed is:

1. A two-part temporomandibular prosthesis, comprising:

a first part and a cooperating second part;

said first part being a prosthetic glenoid fossa including an inferior plate having a fossa cavity defined by a posterior rim, a medial rim, a lateral rim, and an anterior rim; said posterior rim projecting inferiorly of said fossa cavity; said medial rim smoothly joining said posterior rim and projecting inferiorly to cover the medial aspect of the natural glenoid fossa and of the adjoining natural articular eminence; and said anterior rim having an apex and projecting anteriorly and obliquely superiorly to cover the remainder of said natural articular eminence;

said fossa cavity having a stress-bearing, articular surface defined by a relatively deep concave surface beginning posteriorly, extending superiorly to an anteriorly-superiorly located concavo-planar surface, and extending anteriorly to a convexo-planar surface;

said second part being a prosthetic condyle comprising a condylar head having a load-transmitting, convexo-planar, articular face; a heel extending backwardly from said face; a toe extending forwardly from said articular face; and an oval sole extending rearwardly from said face and smoothly blending at its opposite ends with said heel and toe; and said convexo-planar articular face of said condylar head engaging said concavo-planar surface of said fossa cavity and establishing therewith, when said condylar head translates and rotates within said fossa cavity, a substantial planar contact area, thereby providing a substantially even load distribution between the engaged planar surfaces of said prosthetic condyle and of said prosthetic fossa.

2. A glenoid fossa prosthesis for use with a prosthetic or natural condyle of a temporomandibular body joint, said condyle comprising a condylar head having a load-transmitting articular face, said fossa prosthesis including:

an inferior plate having a fossa cavity defined by a posterior rim, a medial rim, a lateral rim, and an anterior rim; said posterior rim projecting inferiorly of said fossa cavity; said medial rim smoothly joining said posterior rim and projecting inferiorly to cover the medial aspect of the natural glenoid fossa and of the adjoining natural articular eminence; and said anterior rim having an apex and projecting anteriorly and obliquely superiorly to cover the remainder of said natural articular eminence;

said fossa cavity having a stress-bearing, articular surface defined by a relatively deep concave surface beginning posteriorly, extending superiorly to an anteriorly-superiorly located concavo-planar surface, and extending anteriorly to a convexo-planar surface; and said articular face of said condylar head engaging said concavo-planar surface of said fossa cavity when said condylar head translates and rotates within said fossa cavity.

3. The two-part temporomandibular prosthesis according to claim 1, wherein
said convexo-planar face of said prosthetic condyle and said concavo-planar surface of said fossa cavity are shaped to maximize the extent of the planar contact areas therebetween.

4. The glenoid fossa prosthesis according to claim 2, wherein
said articular face of said condylar head and said articular surface of said fossa cavity are shaped to maximize the extent of the planar contact areas therebetween.

5. A condylar prosthesis for use with a prosthetic or natural glenoid fossa of a temporomandibular body joint, said prosthetic fossa defining a fossa cavity having a stress-bearing articular surface, said condylar prosthesis, including:
 a condylar head having a load-transmitting, convexo-planar, articular face;
 a heel extending backwardly from said face;
 a toe extending forwardly from said face;
 an oval sole extending rearwardly from said face and smoothly blending at its opposite ends with said heel and toe; and
 said articular face of said condylar head engaging said articular surface of said fossa cavity when said condylar head translates and rotates within said fossa cavity.

* * * * *